United States Patent [19]

Abramovitch et al.

[11] 4,006,160
[45] Feb. 1, 1977

[54] PROCESS FOR THE SYNTHESIS OF N-HYDROXYPYRROLES, N-HYDROXYIMIDAZOLES, AND DERIVATIVES THEREOF

[75] Inventors: Rudolph Abraham Abramovitch; Berkeley Wendell Cue, Jr., both of Tuscoloosa, Ala.

[73] Assignee: University of Alabama, University, Ala.

[22] Filed: May 19, 1975

[21] Appl. No.: 578,895

Related U.S. Application Data

[62] Division of Ser. No. 341,663, March 15, 1973, Pat. No. 3,886,180.

[52] U.S. Cl. .............................. 260/309; 260/309.2; 424/273
[51] Int. Cl.² .............. C07D 233/90; C07D 235/24
[58] Field of Search .................... 260/309, 309.2

[56] References Cited

UNITED STATES PATENTS 3,812,171  5/1974  Neikam et al. ............... 260/326.62
3,850,953  11/1974  Mamalis et al. .................. 260/309

OTHER PUBLICATIONS

Hayashi et al. J. Pharm. Soc. Japan 1962, vol. 82, pp. 1093–1102.

Ikekawa et al. Tetrahedron Letters, 1967, pp. 1197–1200.
Takahashi et al. Chem. Pharm. 1968, vol. 16, pp. 527–538.

*Primary Examiner*—Natalie Trousof
*Attorney, Agent, or Firm*—Oblon, Fisher, Spivak, McClelland & Maier

[57] ABSTRACT

A process is described for the preparation of N-hydroxypyrrole-2-carbonitriles, N-hydroxyimidazole-2-carbonitriles, pyrrole-2-carbonitriles, and 3-substituted-2,3-dihydro-2-pyrrolones by thermally decomposing 2-azidoheteroaromatic N-oxides. In the process a 2-azidoheteroaromatic N-oxide is heated in a suitable solvent for a period of time sufficient to bring the reaction to completion. Removal of the solvent by conventional methods gives the desired product. Which product is obtained is determined by the choice of solvents. In non-polar aprotic solvents, N-hydroxypyrrole-2-carbonitriles or N-hydroxyimidazole-2-carbonitriles are obtained. In nucleophilic solvents capable of undergoing Michael-type additions pyrrole-2-carbonitriles, imidazole-2-carbonitriles, and 3-substituted-2,3-dihydro-2-pyrrolone derivatives are obtained where a solvent molecule comprises the 3-substituent. These compounds are useful as anti-bacterials, e.g., against *E. Coli.*

1 Claim, No Drawings

PROCESS FOR THE SYNTHESIS OF N-HYDROXYPYRROLES, N-HYDROXYIMIDAZOLES, AND DERIVATIVES THEREOF

BRIEF DESCRIPTION OF THE INVENTION

This is a division of application Ser. No. 341,663, filed Mar. 15, 1973, now U.S. Pat. No. 3,886,180.

The present invention relates to N-hydroxypyrroles, N-hydroxyimidazoles and their derivatives. In addition, the present invention also includes within its scope novel processes for the production of these compounds.

In carrying out the process of the invention, the starting 2-azidoheteroaromatic N-oxide is prepared by treatment of the diazonium salt of a 2-aminoheteroaromatic N-oxide, which is prepared by conventional procedures, with sodium azide or by treatment of 2-haloheteroaromatic N-oxides with sodium azide. The 2-azidoheteroaromatic N-oxides thus prepared are dissolved in an appropriate solvent. The solution thus prepared is heated to a temperature above the decomposition temperature of the azide under anhydrous conditions for a period of time sufficient to cause the 2-azidoheteroaromatic N-oxide to decompose completely. When the reaction has reached completion, the N-hydroxypyrrole-2-carbonitrile, N-hydroxyimidazole-2-carbonitrile, pyrrole-2-carbonitrile or 3-substituted-2,3-dihydro-2-pyrrolone derivative can be recovered by conventional procedures. Subsequently, N-hydroxypyrrole-2-carbonitriles and N-hydroxyimidazole-2-carbonitriles can be converted to derivatives suitable for other synthetic manipulation by treatment of such compounds with reagents noted for their ability to act as protecting groups for hydroxyl functions. Such reactions are carried out in aprotic solvents under anhydrous conditions in the presence of a base such as a tertiary aromatic amine. Alternatively, N-hydroxypyrrole-2-carbonitriles can be converted to pyrrole-2-carbonitriles by simply heating them in methanol at about 95° C. for a period of time sufficient to bring the reaction to completion.

DETAILED DESCRIPTION

The present invention provides a practical and commercially feasible method for producing compounds of the formula:

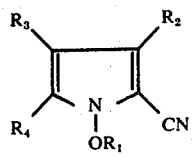

(I)

in which $R_1$ represents an alkyl group, an aroyl group preferably benzoyl, a sulfonyl group, or a trimethylsilyl group, or hydrogen; $R_2$ represents hydrogen, an alkyl group, an aryl group preferably phenyl, or halogen; the symbol $R_3$ represents hydrogen, an alkyl group, an aryl group preferably phenyl, or halogen; and $R_4$ represents hydrogen, halogen, an alkyl group or an aryl group preferably phenyl, or $R_2$ and $R_3$ or $R_3$ and $R_4$ might comprise part of fused aromatic or heteroaromatic ring system, e.g., phenyl, pyridyl and the like.

This process also allows the preparation of compounds having the formula:

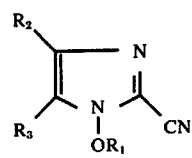

(II)

in which $R_1$ represents hydrogen, an alkyl group, or a sulfonyl group; $R_2$ represents hydrogen, an alkyl group or an aryl group; and $R_3$ represents hydrogen, an alkyl group or an aryl group or $R_2$ and $R_3$ comprise part of an aromatic or heteroaromatic ring.

This process also allows the preparation of compounds having the formula:

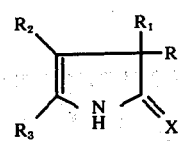

(III)

in which X represents oxygen or an alkyl- or aryl-substituted nitrogen atom; R represents an alkyl- or aryl-substituted tertiary or secondary amine, or an alkoxy group; $R_1$ represents hydrogen, an alkyl group or an aryl group; $R_2$ represents hydrogen, an alkyl group, an aryl group, an alkyl- or arylamino group, or halogen; and $R_3$ represents hydrogen, an alkyl group, or an aryl group.

In the process, a 2-azidoheteroaromatic N-oxide having the formula:

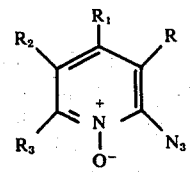

(IV)

in which R represents hydrogen, an alkyl group, an aryl group, or a nitro group; $R_1$ represents hydrogen, an alkyl group, an aryl group, or a nitro group; $R_2$ represents hydrogen, an alkyl group, an aryl group, a nitro group or halogen; $R_3$ represents hydrogen, an alkyl group, or an aryl group is prepared from the diazonium salt of a 2-aminoheteroaromatic-N-oxide having the formula:

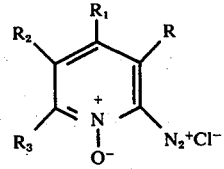

(IVa)

in which the symbols R, $R_1$, $R_2$ and $R_3$ represent substituents referred to (IV) above, and sodium azide in an acidic aqueous medium below 5° C. or is prepared by a reaction between sodium azide and a suitable 2-haloheteroaromatic N-oxide having the formula:

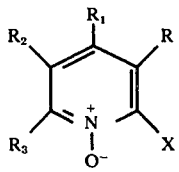

(V)

in which the symbol X represents chlorine or bromine and R, $R_1$, $R_2$, and $R_3$ represent substituents referred to (IV) above. Such azides may be isolated by conventional procedures or may be introduced into a suitable solvent for reaction by extraction from the medium in which they are prepared.

In the process a 2-azidoheteroaromatic N-oxide having the formula:

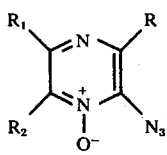

(VI)

in which R represents hydrogen, an alkyl group or an aryl group; $R_1$ represents hydrogen, an alkyl group or an aryl group; $R_3$ represents hydrogen, an alkyl group or an aryl group is prepared from the diazonium salt of a 2-aminoheteroaromatic N-oxide having the formula:

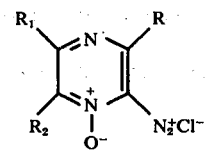

(VII)

in which the symbols R, $R_1$ and $R_2$ refer to those symbols represented in formula VI by reacting said diazonium salt with aqueous sodium azide in an acidic aqueous medium at 0° C. to 5° C., said diazonium salt being prepared by conventional methods.

In carrying out the process of the invention a 2-azidoheteroaromatic N-oxide having the formula:

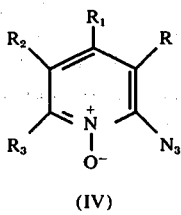 or 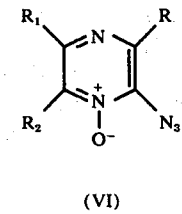

(IV)          (VI)

in which R represents hydrogen and $R_1$, $R_2$ and $R_3$ represent hydrogen, an alkyl group, an aryl group, a nitro group, or halogen is added to and dissolved in a suitable solvent, such as benzene if N-hydroxypyrrole-2-carbonitriles or N-hydroxyimidazole-2-carbonitriles are desired or in an alcohol, a primary amine or a secondary amine if a 3-substituted-2,3-dihydro-2-pyrrolone derivative is desired. The solution thus obtained is heated under an anhydrous atmosphere generally between 80° C. to 100° C. for a period of time necessary to bring the reaction to completion. The product obtained by the reaction of the Formula IV compound in benzene is a pyrrole having the formula:

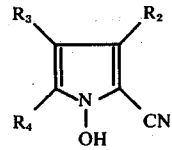

in which $R_2$, $R_3$ and $R_4$ have the same meaning as in the Formula I compound. The product obtained by the reaction of the Formula VI compound in benzene is an imidazole having the formula:

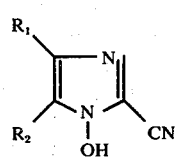

in which the symbols $R_1$ and $R_2$ have the same meaning as in the Formula II compound. The product obtained by the reaction of the Formula IV compound in a nucleophilic solvent capable of undergoing a Michael-type addition such as an alcohol, a primary amine or a secondary amine is a pyrrolone having the formula:

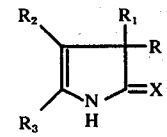

in which the symbols R; $R_1$; $R_2$, $R_3$ and X have the same meaning as in the Formula III. The product obtained by the deoxygenation of the Formula I compound in hot methanol is a pyrrole-2-carbonitrile having the general formula:

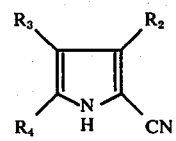

in which the symbols $R_2$, $R_3$, and $R_4$ have the same meaning as in the Formula I compound.

Exemplary of the 2-aminoheteroaromatic N-oxides which are precursors to the novel 2-azidoheteroaromatic N-oxides are 2-aminopyridine N-oxide, 2-amino-3-methylpyridine N-oxide, 2-amino-4-methylpyridine N-oxide, 2-amino-5-methylpyridine N-oxide, 2-amino-6-methylpyridine-N-oxide, 2-amino-5-chloropyridine N-oxide, 2-aminopyrazine-1-oxide, 2-aminoquinoline-1-oxide as well as 2-aminoquinoline-1-oxides, 2-aminopyrimidine-1-oxides, etc.

The 2-haloheteroaromatic N-oxides of Formula V are also known compounds. Exemplary of such compounds are 2-chloropyridine N-oxide, 2-bromopyridine N-oxide, 2-chloro-3-nitropyridine N-oxide, 2-chloro-5-nitropyridine N-oxide, 2-chloroquinoline-1-oxide, 2-chloro-4-nitroquinoline-1-oxide, 2-chloroquinoxaline-1-oxide, 2-chloropyrazine-1-oxide, etc.

The pyrrole-2-carbonitriles of the general formula:

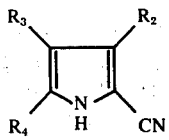

are known compounds. Exemplary of such compounds are pyrrole-2-carbonitrile, 3-methylpyrrole-2-carbonitrile, 4-methylpyrrole-2-carbonitrile, 5-methylpyrrole-2-carbonitrile, 6-methylpyrrole-2-carbonitrile. However, such compounds have previously been obtained only with difficulty and usually as mixtures of isomers.

The compounds of this invention, typically the N-hydroxypyrrole-2-carbonitriles are useful as anti-bacterials. For example, 4-chloro-N-hydroxypyrrole-2-carbonitriles exhibit bactericidal activity against micrococcus and *E. Coli.* in concentrations between 10 and 20 mcg. per ml. These compounds are therefore useful in treating bacterial infections caused by these organisms. For example, to treat skin infections caused by micrococcus, from 0.1% by weight to 1% by weight of the compound is mixed with a vehicle such as talc or white petrolatum and applied liberally to the infected site.

For a fuller understanding of the nature and objects of this invention, reference may be made to the following examples which are given merely as further illustrations of the invention and are not to be construed in a limiting sense.

EXAMPLE 1

In this example, 3.00 grams (0.0205 mol) of 2-amino-pyridine N-oxide hydrochloride was dissolved in 50 ml. of water and 4 ml. of concentrated hydrochloric acid with vigorous stirring and cooled in a salt-ice bath to a temperature between 0.5° C. To the above solution, a solution of 1.41 grams (0.0204 mol) of sodium nitrite in 10 ml. of water was added dropwise at such a rate that the temperature of the reaction mixture did not rise above 5° C. Immediately after addition of the sodium nitrite solution was complete, a solution of 1.35 grams (0.0208 mol) of sodium azide in 10 ml. of water was added dropwise to the reaction mixture at such a rate that the temperature of the reaction mixture did not rise above 5° C. When the addition of the aqueous sodium azide solution was complete, the ice bath was removed and the reaction mixture was warmed to about 25°. The reaction mixture was extracted continuously with methylene chloride to give, after evaporation of the methylene chloride at reduced pressure below 50° C., 2-azidopyridine N-oxide in a yield of 2.05 grams or 70% of theory, having a melting point of 83.5° to 84.5° C. (decomposition).

Calculated for $C_5H_4N_4O$: Calcd: C, 44.12; H, 2.96. Found: C, 44.37; H, 3.10.

EXAMPLE 2

In this example, 16.05 grams (0.100 mol) of 2-amino-3-methylpyridine N-oxide hydrochloride was added to and dissolved in 300 ml. of water and 25 ml. of concentrated hydrochloric acid with vigorous stirring and the above solution cooled to 0°–5° C. in a salt-ice bath. To the above solution, a solution of 6.90 grams (0.100 mol) of sodium nitrite in 100 ml. of water was added dropwise at such a rate that the temperature of the reaction mixture did not rise above 5° C. Immediately after completion of the above addition, a solution of 6.50 grams (0.100 mol) of sodium azide in 100 ml. of water was added at such a rate that the temperature of the reaction mixture did not rise above 5° C. When the addition of the aqueous sodium azide solution was complete the ice bath was removed and the reaction mixture was slowly warmed to about 25° C. The reaction mixture was continuously extracted with methylene chloride to give, after evaporation of the methylene chloride in vacuo below 50° C., 2-azido-3-methylpyridine N-oxide in a yield of 10.80 grams or 72% of theory having a melting point of 89° C. to 90° C. (decomposition).

Calculated for $C_6H_6N_4O$: Calcd: C, 48.00; H, 4.00. Found: C, 48.18; H, 4.22.

EXAMPLE 3

In this example, 12.50 grams (0.0780 mol) of 2-amino-4-methylpyridine N-oxide hydrochloride was added to and dissolved in 250 ml. of water and 20 ml. of concentrated hydrochloric acid with vigorous stirring and the above solution was cooled to 0°–5° C. in a salt-ice bath. To the above solution, 5.67 grams (0.0820 mol) of sodium nitrite in 50 ml. of water was added dropwise at such a rate that the temperature of the reaction mixture did not rise above 5° C. Immediately after completion of the above addition a solution of 5.30 grams (0.0820 mol) of sodium azide in 50 ml. of water was added at such a rate that the temperature did not rise above 5° C. When this addition was complete, the cooling bath was removed and the reaction mixture was slowly warmed to about 25° C. The reaction mixture was continuously extracted with methylene chloride to give, after evaporation of the methylene chloride in vacuo below 50° C., 2-azido-4-methylpyridine N-oxide in a yield of 9.20 grams or 80% of theory having a melting point of 54° C.–56° C. (decomposition).

Calculated for $C_6H_6N_4O$: Calcd: C, 48.00; H, 4.00. Found: C, 48.26; H, 4.15.

EXAMPLE 4

In this example, 7.00 grams (0.0460 mol) of 2-amino-5-methylpyridine N-oxide hydrochloride was added to and dissolved in 100 ml. of water and 10 ml. of concentrated hydrochloric acid with vigorous stirring and the above solution was cooled in a salt-ice bath to 0°–5° C. To the above solution, 3.20 grams (0.0460 mol) of sodium nitrite in 20 ml. of water was added dropwise at such a rate that the temperature of the reaction mixture did not rise above 5° C. Immediately after completion of the above addition, a solution of 3.00 grams (0.0460 mol) of sodium azide in 20 ml. of water was added at such a rate that the temperature of the reaction mixture did not rise above 5° C. When this addition was complete the cooling bath was removed and the reaction mixture slowly warmed to about 25° C. The reaction mixture was extracted continuously with methylene chloride to give, after evaporation of the methylene chloride in vacuo below 50° C., 2-azido-5-methylpyridine N-oxide in a yield of 3.58 grams or 52% of theory having a melting point of 68° C. to 69° C. with decomposition.

Calculated for $C_6H_6N_4O$: Calcd: C, 48.00; H, 4.00. Found: C, 48.26; H, 4.21.

EXAMPLE 5

In this example, 9.00 grams (0.056 mol) of 2-amino-6-methylpyridine N-oxide hydrochloride was added to and dissolved in 100 ml. of water and 10 ml. of concentrated hydrochloric acid with vigorous stirring and was cooled in a salt-ice bath to 0° to 5° C. To the above solution 3.90 grams (0.056 mol) of sodium nitrite in 20 ml. of water was added dropwise at such a rate that the temperature of the reaction mixture did not rise above 5° C. Immediately after completion of the above addition, a solution of 3.50 grams (0.056 mol) of sodium azide in 20 ml. of water was added to the cold vigorously stirred reaction mixture at such a rate that the temperature did not rise above 5° C. When the above addition was complete, the cooling bath was removed and the reaction mixture was slowly warmed to about 25° C. The reaction mixture was extracted with methylene chloride. There was thus obtained from the methylene chloride extract after careful evaporation 2-azido-6-methylpyridine N-oxide in a yield of 6.00 grams or 72% of theory having a melting point of 43° C. to 46° C. with decomposition.

Calculated for $C_6H_6N_4O$: Calcd: C, 48.00; H, 4.00. Found: C, 48.18; H, 4.20.

EXAMPLE 6

In this example, 6.70 grams (0.036 mol) of 2-amino-5-chloropyridine N-oxide hydrochloride was added to and dissolved in 100 ml. of water and 10 ml. of concentrated hydrochloric acid under vigorous stirring and was thus cooled to 0° C. to 5° C. in a salt-ice bath. To the above cold solution, a solution of 2.50 grams (0.036 mol) in 30 ml. of water was added dropwise at such a rate that the temperature of the reaction mixture did not rise above 5° C. Immediately after the above addition was complete a solution of 2.30 grams (0.036 mol) of sodium azide in 30 ml. of water was added to the cold vigorously stirred above solution at such a rate that the temperature did not rise above 5° C. When the above addition was complete the cooling bath was removed and the solution slowly warmed to about 25° C. The reaction mixture was continuously extracted with methylene chloride. From the methylene chloride extract, after evaporation in vacuo was obtained 2-azido-5-chloropyridine N-oxide in a yield of 3.75 grams or 62% of theory having a melting point of 80° C. to 82° C. with decomposition.

Calculated for $C_5H_3N_4OCl$: Calcd: C, 35.19; H, 1.76. Found: C, 35.12; H, 1.76.

EXAMPLE 7

In this example, 1.20 grams (0.007 mol) of 2-chloro-3-nitropyridine N-oxide and 0.914 gram (0.014 mol) sodium azide was added to and dissolved in 10 ml. of water and 25 ml. of acetone. The solution was stirred at about 25° C. for 72 hours. The acetone portion of the above solution was removed in vacuo and the aqueous solution thus obtained was extracted with methylene chloride to give, after evaporation of the methylene chloride, 2-azido-3-nitropyridine N-oxide in a yield of 0.855 grams or 69% of theory having a melting point of 85.5° C. to 87.5° C. with decomposition.

Calculated for $C_5H_3N_5O_3$: Calcd: C, 33.15; H, 1.66. Found: C, 33.39; H, 1.86.

EXAMPLE 8

In this example, 2.50 grams (0.014 mol) of 2-chloro-5-nitropyridine N-oxide and 2.00 grams (0.030 mol) of sodium azide were added to and dissolved in 40 ml. of water and 120 ml. of acetone. The above solution was stirred at 25° C. for about 48 hours. The acetone was removed by vacuum distillation. The aqueous phase was extracted with methylene chloride to give, after evaporation of the methylene chloride in vacuo, 2-azido-5-nitropyridine N-oxide in a yield of 2.00 grams or 80% of theory having a melting point of 118° C. to 119° C. with decomposition.

Calculated for $C_5H_3N_5O_3$: Calcd: C, 33.15; H, 1.66. Found: C, 33.12; H, 1.69.

EXAMPLE 9

In this example, 2.00 grams (0.009 mol) of 2-chloroquinoline N-oxide hydrochloride and 2.00 grams (0.031 mol) of sodium azide were added to and dissolved in 50 ml. of water and 100 ml. of acetone and the resulting solution stirred for 72 hours at 25° C. A solid separated and was collected by filtration. Recrystallization of this solid from benzene gave 2-azidoquinoline N-oxide in a yield of 1.01 grams or 58% of theory having a melting point of 103.5° C. to 104.5° C. with decomposition.

Calculated for $C_9H_6N_4O$: Calcd: C, 58.07; H, 3.22. Found: C, 57.94; H, 3.45.

EXAMPLE 10

In this example, 0.305 grams (0.0021 mol) of 2-aminopyrazine N-oxide hydrochloride was added to and dissolved in 20 ml. of water and 2 ml. of concentrated hydrochloric acid and with vigorous stirring cooled to 0° C. to 5° C. in a salt-ice bath. To the above solution 0.145 grams (0.0021 mol) of sodium nitrite in 10 ml. of water was added at such a rate that the temperature did not rise above 5° C. Next, 0.135 grams (0.0021 mol) of sodium azide in 10 ml. of water was added to the above solution at such a rate that the temperature did not rise above 5° C. When the above addition was complete, the cooling bath was removed and the solution slowly warmed to about 25° C. The reaction mixture was extracted with methylene chloride to give, after evaporation of the solvent, 2-azidopyrazine N-oxide in a yield of 0.071 grams or 25% of theory having a melting point of 85° C. to 87° C. with decomposition.

Calculated for $C_4H_3N_5O$: Calcd: C, 35.04; H, 2.19.

EXAMPLE 11

In this example, 1.070 grams (0.0078 mol) of 2-azidopyridine N-oxide was added to and dissolved in 20 ml. of benzene and the resulting solution was heated in an oil bath under a dry nitrogen atmosphere in a sealed tube at 90° for 8 hours. Evaporation of the solvent gave a residue which was purified by vacuum distillation. There was thus obtained N-hydroxypyrrole-2-carbonitrile in a yield of 0.762 grams or 90% of theory, having a boiling point of 80° C. to 82° C. at 0.500 mm. of mercury.

Calculated for $C_5H_4N_2O$: Calcd: MW, 108.0324. Found: MW, 108.0326; (high resolution Mass spectrometry).

EXAMPLE 12

In this example, 0.530 grams (0.0035 mol) of 2-azido-6-methylpyridine N-oxide was added to and dissolved in 10 ml. of benzene and the resulting solution heated under a dry nitrogen atmosphere at 90° C. in a sealed tube for 8 hours. Evaporation of the solvent gave a residue which was purified by vacuum distillation. There was thus obtained N-hydroxy-5-methylpyrrole-2-carbonitrile in a yield of 0.315 grams or 74% of theory, having a boiling point of 103° C. to 105° C. at 0.500 mm. of mercury.

Calculated for $C_6H_6N_2O$: Calcd: C, 59.01; H, 4.91. Found: C, 59.12; H, 5.04.

EXAMPLE 13

In this example, 3.00 grams (0.020 mol) of 2-azido-4-methylpyridine N-oxide was added to and dissolved in 40 ml of benzene and the resulting solution was heated under a dry nitrogen atmosphere in an oil bath at 85° C for 12 hours. Evaporation of the solvent in vacuo gave a residue which was purified by vacuum distillation. There was thus obtained N-hydroxy-3-methylpyrrole-2-carbonitrile in a yield of 1.05 grams or 43.5% of theory having a melting point of 58° C to 60° C.

Calculated for $C_6H_6N_2O$: Calcd: C, 59.01; H, 4.92. Found: C, 59.32; H, 5.05.

EXAMPLE 14

In this example, 1.533 grams (0.0102 mol) of 2-azido-5-methylpyridine N-oxide was added to and dissolved in 30 ml of benzene. The resulting solution was heated in an oil bath in a sealed tube under a dry nitrogen atmosphere at 85° C for 8 hours. Evaporation of the solvent gave a residue which was purified by sublimation. There was thus obtained N-hydroxy-4-methylpyrrole-2-carbonitrile in a yield of 0.725 grams or 59% of theory, having a melting point of 58° C to 60° C.

Calculated for $C_6H_6N_2O$: Calcd: MW, 122.0480. Found: MW, 122.0480; (high resolution mass spectrometry).

EXAMPLE 15

In this example, 0.873 grams (0.005 mol) of 2-azido-5-chloropyridine N-oxide was added to and dissolved in 10 ml of benzene. The resulting solution was heated in a sealed tube at 95° C for 11 hours under a dry nitrogen atmosphere. Evaporation of the solvent gave a residue which was purified by recrystallization from benzene. There was thus obtained N-hydroxy-4-chloropyrrole-2-carbonitrile in a yield of 0.601 grams or 82% of theory having a melting point of 102° C to 103° C with decomposition.

Calculated for $C_5H_3ClN_2O$: Calcd: C, 42.10; H, 2.10. Found: C, 42.34; H, 2.10.

EXAMPLE 16

In this example, 1.085 grams (0.008 mol) of 2-azidopyridine N-oxide was added to and dissolved in 20 ml of methanol. The resulting solution was heated in a sealed tube under a dry nitrogen atmosphere for 18 hours in an oil bath at 95° C. Evaporation of the solvent under vacuum gave an oil which was purified by fractional distillation. There was thus obtained pyrrole-2-carbonitrile in a yield of 0.044 grams or 5% of theory and 3-methoxy-2,3-dihydro-2-pyrrolone in a yield of 0.208 grams or 23% of theory, having a melting point of 50° to 52° C.

Calculated for $C_5H_7NO_2$: Calcd: 53.10; H, 6.20. Found: 52.94; H, 6.26.

EXAMPLE 17

In this example, 1.00 grams (0.0058 mol) of 2-azido-5-chloropyridine N-oxide was added to and dissolved in 20 ml of methanol. The resulting solution was heated under a dry nitrogen atmosphere in a sealed tube in an oil bath at 90° C for 12 hours. Evaporation of the solvent gave a residue which was purified by preparative column chromatography on silica. Elution with benzene gave 4-chloropyrrole-2-carbonitrile in a yield of 0.035 grams or 5% of theory having a melting point of 71° C to 73° C. Elution with chloroform gave 4-chloro-3-methoxy-2,3-dihydro-2-pyrrolone in a yield of 0.256 grams or 28% of theory having a melting point of 96° C to 98° C.

Calculated for $C_5H_6ClN_2O$: Calcd: C, 40.68; H, 4.07. Found: C, 41.00; H, 4.42.

EXAMPLE 18

In this example, 0.415 grams (0.003 mol) of 4-chloro-N-hydroxy-pyrrole-2-carbonitrile was added to and dissolved in 20 ml of methanol. The resulting solution was heated under a dry nitrogen atmosphere in a sealed tube at 90° C for 20 hours. Evaporation of the methanol in vacuo gave a residue which was recrystallized from hexane. There was thus obtained 4-chloropyrrole-2-carbonitrile in a yield of 0.228 grams or 60% of theory having a melting point of 71° C to 73° C.

Calculated for $C_5H_3ClN_2$: Calcd: C, 47.46; H, 2.38. Found: C, 47.75; H, 2.68.

EXAMPLE 19

In this example, 2.00 grams (0.0162 mol) of 2-azidopyridine N-oxide was added to and dissolved in 20 ml of aniline. The resulting solution was heated under a dry nitrogen atmosphere in a sealed tube at 85° C for 12 hours. Evaporation of the solvent in vacuo gave a residue which was purified by preparative column chromatography on silica. Elution with benzene gave pyrrole-2-carbonitrile in a yield of 0.039 grams or 22% of theory. Elution with chloroform/ether (1:1) gave 3-anilino-2,3-dihydro-2-pyrrolone N-phenylimine in a yield of 1.11 grams or 26% of theory, having a melting point of 137° C to 139° C.

Calcd for $C_{16}H_{15}N_3$: Calcd: C, 77.11; H, 6.02.

Elution with ethanol gave 2-aminopyridine N-oxide in a yield of 0.426 grams or 24% of theory having a melting point of 158° C to 159.5° C.

EXAMPLE 20

In this example, 0.045 grams (0.00033 mol) of 2-azidopyrazine N-oxide was added to and dissolved in 5 ml of benzene. The above solution was heated in a sealed tube under a dry nitrogen atmosphere at 85° C for 3 hours. Evaporation of the solvent gave N-hydroxyimidazole-2-carbonitrile in a yield of 0.030 grams or 83% of theory having a melting point of 159° C to 161° C.

Calculated for $C_4H_3N_3O$: Calcd: C, 44.04; H, 2.75.

EXAMPLE 21

In this example, 0.120 grams (0.0011 mol) of N-hydroxypyrrole-2-carbonitrile and 2.415 grams (0.0022 mol) of p-toluenesulfonylchloride were added to and dissolved in 20 ml of methylene chloride and 0.5 ml of pyridine. The resulting solution was stirred under a dry nitrogen atmosphere at 25° C for 24 hours. The reaction mixture was treated with 20 ml of ice cold aqueous 10% hydrochloric acid, then 20 ml of cold aqueous sodium carbonate, discarding the aqueous phase in each case. The organic phase was evaporated to give N-(p-toluenesulfonyloxy)-2-carbonitrile in a yield of 0.259 grams or 90% of theory having a melting point of 79.5° C to 80.5° C with decomposition.

Calculated for $C_{12}H_{10}N_2O_3S$: Calcd: C, 54.92; H, 3.82. Found: C, 54.92; H, 4.04.

EXAMPLE 22

In this example, 0.130 grams (0.0012 mol) of N-hydroxypyrrole-2-carbonitrile and 0.428 grams (0.0025 mol) of p-nitrobenzyl chloride were added to and dissolved in 25 ml of dry chloroform and 0.5 ml of pyridine. The above solution was stirred under a dry nitrogen atmosphere for 48 hours at 25° C. To this solution 10 ml of a saturated aqueous solution of potassium carbonate was added and stirring was continued for another 24 hours, and the solution extracted with chloroform. The aqueous phase was discarded and the chloroform extract evaporated to give a residue which was chromatographed on silica. After washing the column with benzene to remove any unreacted p-nitrobenzyl chloride. Column was washed with chloroform to give N-(p-nitrobenzyloxy)pyrrole-2-carbonitrile in a yield of 0.218 grams or 75% of theory having a melting point of 69° C to 70° C.

Calculated for $C_{12}H_9N_3O_3$: Calcd: C, 59.26; H, 3.70. Found: C, 59.40; H, 3.88.

EXAMPLE 23

In this example, 0.425 grams (0.0039 mol) of N-hydroxypyrrole-2-carbonitrile and 1.02 grams (0.0073 mol) of benzoyl chloride were added to and dissolved in 30 ml of benzene and 1 ml of pyridine. The solution was heated at reflux temperature for 12 hours. Water was added to hydrolyze any unreacted benzoyl chloride. The mixture was washed with 20 ml of 20% hydrochloric acid, then with 20 ml of 20% aqueous potassium carbonate, the aqueous layers being discarded after each washing. The organic phase was evaporated in vacuo to give N-benzoyloxypyrrole-2-carbonitrile in a yield of 0.508 grams or 62% of theory having a melting point of 81° C to 82° C.

Calculated for $C_{12}H_8N_2O_2$: Calcd: C, 67.92; H, 3.78. Found: C, 67.98; H, 3.95.

EXAMPLE 24

In this example, 0.067 grams (0.0005 mol) of N-hydroxy-5-methylpyrrole-2-carbonitrile and 0.190 grams (0.0010 mol) of p-toluenesulfonyl chloride were added to and dissolved in 10 ml of methylene chloride and 0.5 ml of pyridine. The solution was stirred at 25° C for 24 hours under a dry nitrogen atmosphere. An equal volume of ice cold water was added and the resulting mixture stirred an additional 24 hours. The solution was diluted with methylene chloride, washed with 20% aqueous hydrochloric acid, then with 10% aqueous sodium carbonate, the aqueous phase being discarded each time. Evaporation of the methylene chloride phase in vacuo gave N-(p-toluenesulfonyloxy)-5-methylpyrrole-2-carbonitrile in a yield of 0.067 grams or 50% of theory having a melting point of 59° C to 61° C.

Calculated for $C_{13}H_{12}N_2O_3S$: Calcd: C, 56.52; H, 4.35. Found: C, 56.78; H, 4.73.

EXAMPLE 25

In this example, 0.386 grams (0.00316 mol) of N-hydroxy-5-methylpyrrole-2-carbonitrile and 1.05 grams (0.0055 mol) of p-nitrobenzyl chloride were added to and dissolved in 75 ml of chloroform and 1 ml of pyridine. The resulting solution was stirred at 25° C for 48 hours under a dry nitrogen atmosphere. An equal volume of saturated aqueous potassium carbonate was added and the resulting solution stirred for 24 hours at 25° C. The organic phase was separated and evaporated in vacuo to give a residue which was chromatographed on silica. After washing the column with benzene to remove any unreacted p-nitrobenzyl chloride the column was washed with chloroform to give N-(p-nitrobenzyloxy)-5-methylpyrrole-2-carbonitrile in a 0.354 gram yield or 44.3% of theory.

Calculated for $C_{13}H_{11}N_3O_3$: Calcd: C, 60.70; H, 4.28. Found: C, 60.64; H, 4.47.

EXAMPLE 26

In this example, 0.076 grams (0.0050 mol) of N-hydroxy-4-chloropyrrole-2-carbonitrile and 1.430 grams (0.0075 mol) of p-toluenesulfonyl chloride were added to and dissolved in 75 ml of chloroform and 2 ml of pyridine. The solution was stirred at 25° C for 48 hours under a dry nitrogen atmosphere. The reaction mixture was treated with 50 ml of ice cold aqueous 10% hydrochloric acid then with 50 ml of cold aqueous 10% sodium carbonate, discarding the aqueous phase in each case. The organic layer was evaporated in vacuo to give N-(p-toluenesulfonyloxy)-4-chloropyrrole-2-carbonitrile in a yield of 0.685 grams or 50% of theory, having a melting point of 101° C to 102° C.

Calculated for $C_{12}H_9ClN_2O_3S$: Calcd: C, 48.23; H, 3.04. Found: C, 48.52; H, 3.12.

EXAMPLE 27

In this example 0.500 grams (0.0028 mol) of 2-chloroquinoxaline 1-oxide and 0.500 grams (0.0080 mol) of sodium azide were added to and dissolved in 35 ml of acetone and 35 ml of water. The solution was stirred at 25° C for 60 hours. The acetone was evaporated in vacuo and the resulting aqueous solution was extracted with methylene chloride. The organic phase was introduced onto a basic alumina column. Elution with chloroform gave 2 azidoquinoxaline-oxide in a yield of 0.080 grams or 16% of theory which was immediately decomposed in boiling benzene for 1 hour. Evaporation of the solvent gave 2-cyanobenzimidazole N-oxide which is tautomeric with N-hydroxy-2-cyanobenzimidazole in a yield of 0.020 grams or 30% of theory having a melting point of 236° C to 238° C with decomposition.

We claim:

1. A process for the production of an N-hydroxyimidazole-2-carbonitrile compound possessing antibacterial activity and having the formula:

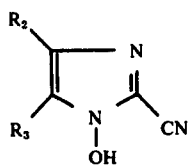

wherein $R_3$ is hydrogen, alkyl or aryl and $R_2$ is hydrogen, alkyl or aryl or $R_3$ and $R_2$ comprise part of a fused aromatic or heteroaromatic nucleus which comprises thermally decomposing a 2-azidopyrazine N-oxide having the formula:

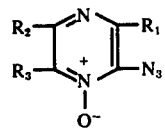

in which $R_1$ is hydrogen, $R_2$ is hydrogen, alkyl or aryl and $R_3$ is hydrogen, alkyl or aryl or where $R_2$ and $R_3$ comprise part of a fused aromatic or heteroaromatic nucleus and said reaction being carried out in an inert solvent at a temperature above the decomposition temperature of the azide, under an anhydrous atmosphere.

* * * * *

UNITED STATES PATENT AND TRADEMARK OFFICE
CERTIFICATE OF CORRECTION

PATENT NO. : 4,006,160
DATED : February 1, 1977
INVENTOR(S) : RUDOLPH A. ABRAMOVITCH ET AL It is certified that error appears in the above-identified patent and that said Letters Patent are hereby corrected as shown below:

In the title page, please correct applicants' place of address from "Tuscoloasa" to --Tuscaloosa--.

In the first two lines of Column 10, insert "C" before numbers --53.10-- and --52.94--.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*